(12) United States Patent
Ibrahim

(10) Patent No.: US 6,415,182 B1
(45) Date of Patent: Jul. 2, 2002

(54) HERMETIC GROUND PIN ASSEMBLY AND METHOD OF MAKING

(75) Inventor: Shawki S. Ibrahim, Tippecanoe, IN (US)

(73) Assignee: CTS Corporation, Elkhart, IN (US)

( * ) Notice: Subject to any disclaimer, the term of this patent is extended or adjusted under 35 U.S.C. 154(b) by 0 days.

(21) Appl. No.: 09/495,220

(22) Filed: Jan. 31, 2000

(51) Int. Cl.[7] ................................................ A61N 1/375
(52) U.S. Cl. ..................... 607/36; 174/50.52; 29/592.1; 228/262.61; 228/262.72
(58) Field of Search ............................... 607/36, 37, 9; 439/909; 228/124.6, 135, 227, 262.6, 262.61, 262.72; 174/50.52, 51, 50.5; 29/592.1

(56) References Cited

U.S. PATENT DOCUMENTS

| | | | |
|---|---|---|---|
| 4,352,951 A | * | 10/1982 | Kyle .................... 174/152 GM |
| 5,368,220 A | * | 11/1994 | Mizuhara et al. ............ 174/263 |
| 5,709,724 A | * | 1/1998 | Naugler et al. ............... 65/59.4 |
| 5,870,272 A | * | 2/1999 | Seifried et al. ...... 174/152 GM |
| 5,871,513 A | | 2/1999 | Taylor et al. |
| 6,031,710 A | * | 2/2000 | Wolf et al. .......... 174/152 GM |
| 6,037,539 A | * | 3/2000 | Kilgo et al. ............. 174/50.61 |

* cited by examiner

Primary Examiner—Kennedy Schaetzle
(74) Attorney, Agent, or Firm—Mark P. Bourgeois; Mark W. Borgman

(57) ABSTRACT

A hermetic ground pin assembly for making an electrical connection between a hermetically sealed enclosure and an external circuit. A case has an aperture and a plug located within the aperture. A low temperature braze alloy is located between the plug and the case to attach the plug within the aperture. Two different pins are attached to opposite sides of the plug. A high temperature braze alloy attaches one of the pins to the plug and the low temperature braze alloy attaches the other pin to the plug.

13 Claims, 2 Drawing Sheets

HERMETIC GROUND PIN ASSEMBLY AND METHOD OF MAKING

BACKGROUND OF THE INVENTION

1. Field of the Invention

This invention relates to a hermetic ground pin assembly for making an electrical connection between a hermetically sealed enclosure and an external circuit.

2. Description of the Related Art

Various devices are well known for conducting an electrical signal. One type of application for signal conduction that is very demanding is in the field of implantable electronic medical devices such as pacemakers, heart pumps and implantable defibrillators. These electronic packages must be of the highest reliability and corrosion resistance as any failure can have potentially lethal consequences. The electronics are hermetically sealed within a case typically made from titanium. The case needs to be grounded to protect the circuitry inside from electromagnetic transients and electrostatic discharge. At the same time, the circuitry inside the case must be electrically isolated from the case and yet be connectable to external circuits such as a battery or signal pins.

In order to insure reliable connections gold plated pins and/or terminals are used. The plating is done after any high temperature processing. Subjecting the plating to high temperatures will destroy the integrity of the plating. Unfortunately, apart from the high cost of gold plating, the case cannot be electroplated due to physiological compatibility problems during contact with human tissue. Therefore, the. case cannot be connected directly to the electrical connectors for electroplating. In prior art designs, a ceramic insert was used to isolate the pins from the case for electroplating. Other methods then had to be employed such as special glass to metals seals around a wire to provide a ground connection after the rest of the assembly was completed. A current unmet need exists for a reliable, low cost, simple and robust hermetic ground pin assembly for making an electrical connection between a hermetically sealed enclosure and an external circuit that allow other terminals to be electroplated and the electronic enclosure to be physiologically compatible with human tissue.

3. Related Art

Examples of patents that are related to the present invention are as follows, and each patent is herein incorporated by reference for the supporting teachings:

U.S. Pat. Ser. No. 5,871,513 is a centerless ground feedthrough pin for an electrical power source in an implantable medical device.

The foregoing patents reflect the state of the art of which the applicant is aware and are tendered with the view toward discharging the applicant's acknowledged duty of candor in disclosing information which may be pertinent in the examination of this application. It is respectfully stipulated, however, that none of these patents teach or render obvious, singly or when considered in combination, the applicants claimed invention.

SUMMARY OF THE INVENTION

It is a feature of the invention to provide a hermetic ground pin assembly for making an electrical connection between a hermetically sealed enclosure and an external circuit.

An additional feature of the invention is to provide a hermetic ground pin assembly for making an electrical path that includes a case or a case having an aperture therethrough and a plug located within the aperture. A low temperature braze alloy is located between the plug and the case for affixing the plug within the aperture. One or more pins are attached to the plug. A high temperature braze alloy is located between the plug and the outer pin for affixing the pin to the plug.

The invention resides not in any one of these features per se, but rather in the particular combination of all of them herein disclosed and claimed and it is distinguished from the prior art in this particular combination of all of its structures for the functions specified. Other features of the present invention will become more clear from the following detailed description of the invention, taken in conjunction with the accompanying drawings and claims, or may be learned by the practice of the invention.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENTS

Figure 1:
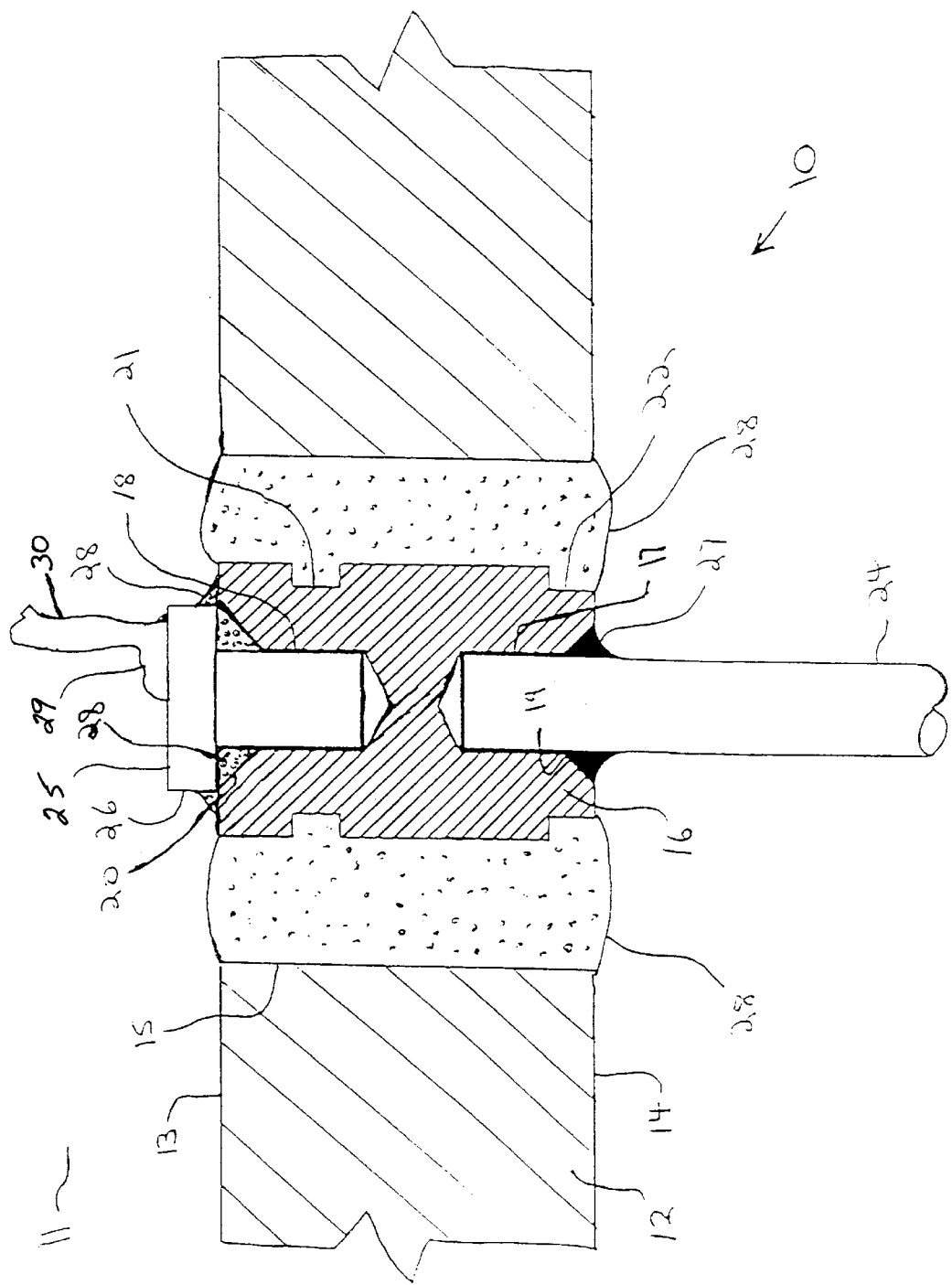
FIG. 1 is a side cross-sectional view of the preffered embodiment of a hermetic ground pin assembly.

Referring to FIG. 1, there is a hermetic ground pin assembly 10 shown. Assembly 10 has a titanium case 12 for containing electronic circuitry (not shown). Case 12 has a cavity 11. Case 12 has an inside surface 13 and an outer surface 14.: An aperture 15 passes through case 12. An annular titanium plug 16 is located in aperture 15 and has a pair of opposed bores, an inner bore 18 and an outer bore 17. Outer bore 17 has a flare 19 and inner bore 18 has a flare 20. A cylindrical inner pin 25 and a cylindrical outer pin 24 are located and affixed into bores 17 and 18, respectively. Outer pin 24 is held by a high temperature braze alloy 27. Inner pin 25 is held by a low temperature braze alloy 28. The outer pin is formed from an alloy of 90% platinum and 10% iridium. The inner pin is formed from 100% nickel so that it can be wire bonded to. Pin 25 has a head 26. A wire 30 is attached to head 26 by a wire bond 29. Wire 30 is an ultrasonically bondable wire such as aluminum or gold. High temperature braze alloy 27 is located in flare 19 between pin 24 and bore 17. The high temperature braze alloy 27 is made up of an alloy that ranges in concentration of 10 to 30 percent nickel and 70 to 90 percent gold by weight. The plug 16 has an annular groove 21 disposed circumferentially and an annular step 22 at one end. The plug 16 is located and affixed into aperture 15 by a low temperature braze alloy 28. Low temperature braze alloy 28 is located between case 12 and plug 16. The pin 25 is located and affixed into bore 18 by low temperature braze alloy 28. The low temperature braze alloy 28 is made up of an alloy that ranges in concentration of 20 to 40 percent copper and 60 to 80 percent silver by weight. Other pins (not shown) are used in the package that are insulated from the case 12 by a ceramic insert (not shown). These pins are the signal pins which are required to be electroplated with gold.

The hermetic ground pin assembly 10 can be assembled in the following manner. First the outer pin 24 is inserted into the plug and the high temperature braze alloy is placed as a preform or otherwise adjacent flare 19. The plug and pin are placed in a fixture and then inserted into a vacuum furnace between 920 and 970 degrees Celsius, such that the high temperature braze melts. The pin and plug is then cooled to room or ambient temperature. The high temperature braze solidifies and pin 24 is fixed into bore 17. Next, the pin 25 is inserted into bore 18 and plug 16 is inserted into aperture 15. A low temperature braze alloy is applied as a preform in the aperture, between the case and the plug and around pin 25 adjacent flare 20. The low temperature braze alloy has a concentration range of 20–40 percent copper and 60–80 percent silver by weight. The case and plug, other signal pins and ceramic spacers are then placed in a fixture and heated in a vaccuum oven to between 760 and 800 degrees Celsius, such that the low temperature braze alloy melts. The assembly 10 is then cooled. The low temperature braze alloy solidifies and the plug 16 and pins are fixed into the aperture. Next, all the other pins in the package besides the ground pin are electroplated with electrolytic nickel and then with gold plating. The package would then have circuitry placed in case 12 for connection to the ground pin using wirebond 29.

Figure 2:
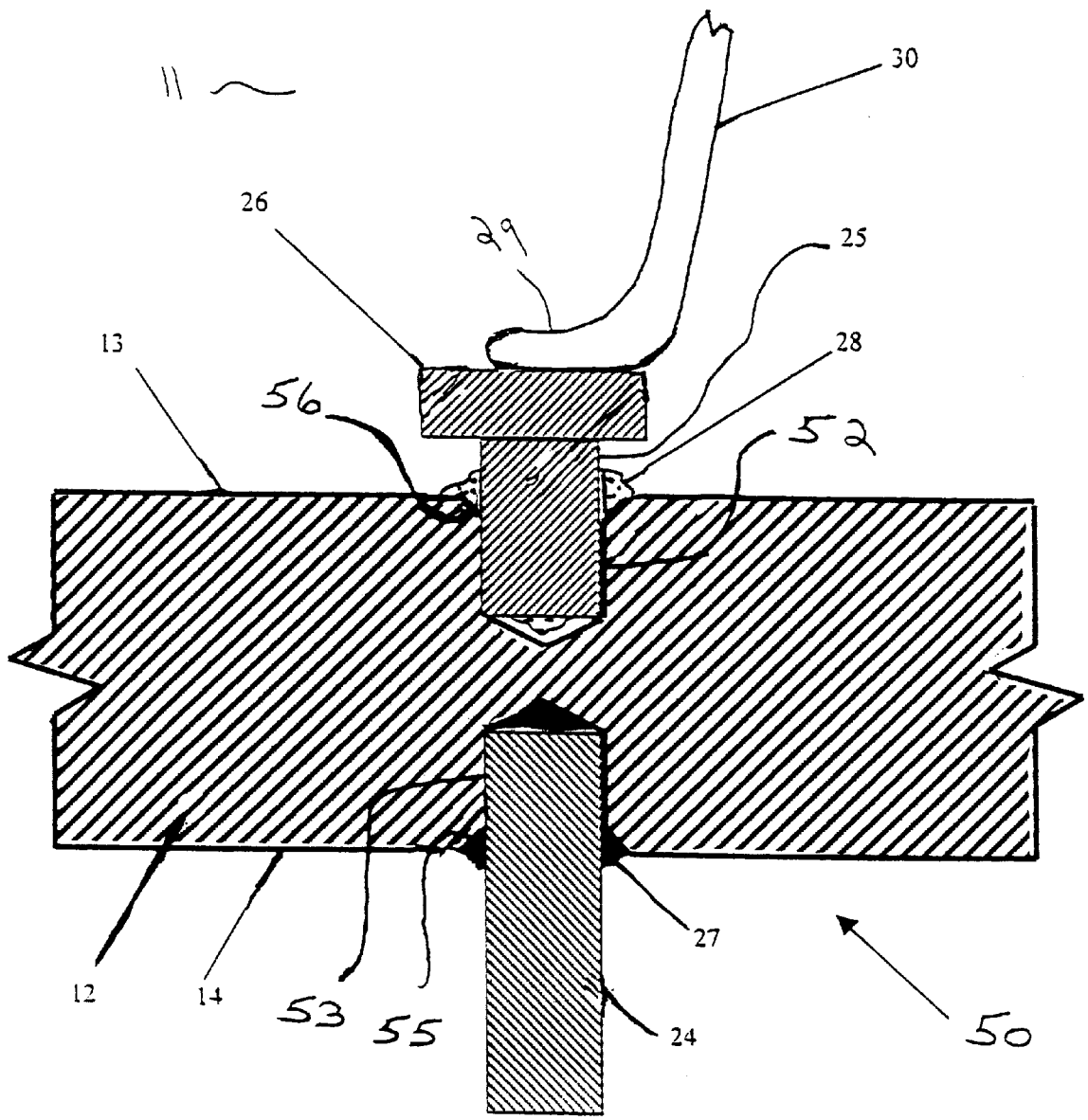
FIG. 2 is a side cross-sectional view of another embodiment of a hermetic ground pin assembly It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. The invention will be described with additional specificity and detail through the use of the accompanying drawings. In the drawings like numbering represents like elements between the drawings.

Referring to FIG. 2, there is another embodiment of a hermetic ground pin assembly 50 shown. Assembly 50 has a titanium case 12 for containing electronic circuitry (not shown). Case 12 has a cavity 11. Case 12 has an inside surface 13 and an outer surface 14. An inner bore 52 and an outer bore 53 are located on inside surface 13 and outer surface 14, respectively. Outer bore 53 has a flare 55 and inner bore 52 has a flare 56. A cylindrical inner pin 25 and a cylindrical outer pin 24 are located and affixed into bores 52 and 53, respectively. Outer pin 24 is held by a high temperature braze alloy 27. Inner pin 25 is held by a low temperature braze alloy 28. The outer pin is formed from an alloy of 90% platinum and 10% irdium. The inner pin is formed from 100% nickel so that it can be wire bonded to. Pin 25 has a head 26. A wire 30 is attached to head 26 by a wire bond 29. Wire 30 is an ultrasonically bondable wire such as aluminum or gold. High temperature braze alloy 27 is located in flare 55 between pin 24 and bore 53. The high temperature braze alloy 27 is made up of an alloy that ranges in concentration of 10 to 30 percent nickel and 70 to 90 percent gold by weight. The pin 25 is located and affixed into bore 52 by low temperature braze alloy 28. The low temperature braze alloy 28 is made up of an alloy that ranges in concentration of 20 to 40 percent copper and 60 to 80 percent silver by weight. Other pins (not shown) are used in the package that are insulated from the case 12 by a ceramic insert (not shown). These pins are the signal pins which are required to be electroplated with gold. Hermetic ground pin assembly 50 is assembled similar to assembly 10, with the high temperature braze alloy melted around outer pin 24 first and then the low temperature braze alloy melted around inner pin 25, next.

Remarks About the Preferred Embodiment

The grounded pin assembly 10 of FIG. 1 allows for an electronic package with the following attributes: A hermetically sealed package. A wire bondable pin on the inside of the case that is not electroplated. A solderable pin on the outside of the case. A titanium case that is free of electroplating. Signal terminals or pins attached to the case that are electroplated with gold.

Variations of the Preferred Embodiment

Although the illustrated embodiment shows the use of a platinum and iddium alloy pin, if desired other types of alloys could be used such as alloys of palladium, gold, silver, rhodium.

The ground pin assembly shown used a low temperature braze alloy and a high temperature braze alloy of a particular composition.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hermetic ground pin assembly for making an electrical path comprising:
   a) a case having an aperture therethrough;
   b) a plug located within the aperture;
   c) a low temperature braze alloy located between the plug and the case for affixing the plug within the aperture;
   d) at least one pin attached to the plug; and
   e) a high temperature braze alloy located between plug and the pin for affixing the pin to the plug.

2. The hermetic ground pin assembly according to claim 1, wherein the plug has a pair of opposed bores having the pins therein.

3. The hermetic ground pin assembly according to claim 2, wherein the low temperature braze alloy has a concentration of 20–40 percent copper and 60–80 percent silver by weight.

4. The hermetic ground pin assembly according to claim 2, wherein the high temperature braze alloy has a concentration of 10–30 percent nickel and 70–90 percent gold by weight.

5. The hermetic ground pin assembly according to claim 3, wherein the pin is an alloy of platinum and iridium.

6. A hermetic ground pin assembly for an implantable medical device comprising:
   a) a case having an aperture;
   b) a plug having a. first and second opposed bores, the plug affixed within the aperture by brazing with a low temperature braze alloy;

c) a first pin affixed in the first bore by brazing with a high temperature braze alloy; and d) a second pin affixed in the second bore by brazing with the low temperature braze alloy.

7. The hermetic ground pin assembly according to claim 6, wherein the low temperature braze alloy has a concentration of 20–40 percent copper and 60–80 percent silver by weight.

8. The hermetic ground pin assembly according to claim 7, wherein the high temperature braze alloy has a concentration of 10–30 percent nickel and 70–90 percent gold by weight.

9. The hermetic ground pin assembly according to claim 8, wherein the first pin is an alloy of platinum and iridium.

10. The hermetic ground pin assembly according to claim 9, wherein the low temperature braze alloy melts between 760 and 800 degrees Celsius.

11. The hermetic ground pin assembly according to claim 10, wherein the high temperature braze alloy melts between 920 and 970 degrees Celsius.

12. A method for making a hermetic ground pin assembly comprising the steps of:

a) providing a case having an aperture therethrough and a plug having a first and second opposed bores;

b) inserting a first pin into the first bore;

c) applying a high temperature braze alloy adjacent the first pin, the high temperature braze alloy having a concentration of 10–30 percent nickel and 70–90 percent gold by weight;

d) heating the first pin, the plug and the high temperature braze alloy to between 920 and 970 degrees Celsius, such that the high temperature braze alloy melts;

e) cooling the first pin, the plug and the high temperature braze alloy to an ambient temperature, such that the high temperature braze alloy solidifies and the first pin is affixed into the first bores;

f) inserting the second pin into the second bore;

g) inserting the plug into the aperture;

g) applying a low temperature braze alloy adjacent the plug and the second pin, the low temperature braze alloy having a concentration of 20–40 percent copper and 60–80 percent silver by weight;

h) heating the case, the pins, the plug and the low temperature braze alloy to between 760 and 800 degrees Celsius, such that the low temperature braze alloy melts; and i) cooling the pins, the plug, the case and the low temperature braze alloy to an ambient temperature, such that the low temperature braze alloy solidifies and the plug and pins are affixed into the aperture.

13. The method of making a hermetic ground pin assembly according to claim 12, wherein the first pin is an alloy of platinum and iridium.

* * * * *